US006048970A

United States Patent [19]
Lal et al.

[11] Patent Number: 6,048,970
[45] Date of Patent: Apr. 11, 2000

[54] PROSTATE GROWTH-ASSOCIATED MEMBRANE PROTEINS

[75] Inventors: Preeti Lal, Santa Clara; Karl J. Guegler, Menlo Park; Neil C. Corley, Mountain View, all of Calif.

[73] Assignee: Incyte Pharmaceuticals, Inc., Palo Alto, Calif.

[21] Appl. No.: 09/083,521

[22] Filed: May 22, 1998

[51] Int. Cl.[7] .......................... C07H 21/04; C07H 21/02; C12N 15/64

[52] U.S. Cl. ...................... 536/23.5; 536/23.1; 536/23.2; 536/23.4; 536/23.31; 435/91.41

[58] Field of Search ................................ 435/69.4, 91.4, 435/91.41; 514/2, 12–19; 530/300–345, 350–385, 412; 536/23.1–24.2, 24.31, 23.5, 25.5

[56] References Cited

PUBLICATIONS

Gattung et al, GenBank Accession 002064, May, 9, 1997.
Strausberg et al, GenBank Accession AA491988, Aug. 19, 1997.
Hillier et al, GenBank Accession RO9227, Apr. 5, 1995.
Strausberg et al, GenBank Accession AA508880, Aug. 13, 1997.
Strausberg et al, GenBank Accession AA177004, Aug. 14, 1997.
Strausberg et al, GenBank Accession AA837043, Feb. 26, 1998.
Hillier et al, GenBank Accession W42412, May 9, 1997.
Hillier et al, GenBank Accession AA171488, Dec. 23, 1996.
Hillier et al, GenBank Accession R38763, Apr. 14, 1995.
Hillier et al, GenBank Accession 18465, Apr. 14, 1995.
Ausubel et al, Current Protocols in Molecular Biology, Chapter 16, pp. 16.0.1 through 16.2.11), 1990.
Helzlsouer, K.J., "Epidemiology, prevention, and early detection of breast cancer", *Curr. Opin. Oncol.*, 6:541–548 (1994).
Harris, J.R. et al., "Breast Cancer", *N. Engl. J. Med.*, 327:319–328 (1992).
Minegishi, M. et al., "Monoclonal Antibody Directed to Human T–Cell Malignancy Antigen", *Leukemia Res.*, 13:43–51 (1989).
Takagi, S. et al., "Indentification of a Highly Specific Surface Marker of T–Cell Acute Lymphoblastic Leukemia and Neuroblastoma as a New Member of the Transmembrane 4 Superfamily", *Int. J. Cancer*, 61:706–715 (1995).
Liu, E. et al., "The HER2 (c–erbB–2) oncogene is frequently amplified in in situ carcinomas of the breast", *Oncogene*, 7:1027–1032 (1992).
Kern, J.A. et al., "Inhibition of Human Lung Cancer Cell Line Growth by an Anti–p185[HER2] Antibody",*Am. J. Respir. Cell Mol. Biol.*, 9:448–454 (1993).

Imai, T. and O. Yoshi, "C33 Antigen and M38 Antigen Recognized by Monoclonal Antibodies Inhibitory to Syncytium Formation by Human T Cell Leukemia Virus Type 1 Are Both Members of the Transmembrane 4 Superfamily and Associate with Each Other and with CD4 or CD8 in T Cells", *J. Immunol.*, 151:6470–6481 (1993).
Hotta, H. et al., "Molecular Cloning and Characterization of an Antigen Associated with Early Stages of Melanoma Tumor Progression", *Cancer Res.*, 48:2955–2962 (1988).
Classon, B.J. et al., "The Primary Structure of the Human Leukocyte Antigen CD37, a Species Homologue of the Rat MRC OX–44 Antigen", *J. Exp. Med.*, 169:1497–1502 (1989).
Tomlinson, M.G. and M.D. Wright, "Characterisation of Mouse CD37: cDNA and Genomic Cloning", *Mol. Immunol.*, 33:867–872 (1996).
Pearson, J.D. and H.B. Carter, "Natural History of Changes in Prostate Specific Antigen in Early Stage Prostate Cancer", *J. Urol.*, 152:1743–1748 (1994).
Asundi, V.K. and K.L. Dreher, "Molecular charaterization of vascular smooth muscle decorin: deduced core protein structure and regulation of gene expression", *Eur. J. Cell Biol.*, 59:314–321 (1992).
Landschulz, W.H. et al., "The Leucin Zipper: A Hypothetical Structure Common to a New Class of DNA Binding Proteins", *Science*, 240:1759–1764 (1988).
Vanhaesebroeck, B. et al., "p110δ, a novel phosphoinositide 3–kinase in leukocytes", *Proc. Natl. Acad. Sci. USA*, 94:4330–4335 (1997).
Thompson, C.B., "Apoptosis in the Pathogenesis and Treatment of Disease", *Science*, 267:1456–1462 (1995).
O'Connor, L. et al., "Bim: a novel member of the Bcl–2 family that promotes apoptosis", *EMBO J.*, 17:384–395 (1998).
Gaozza, E. et al., (Direct Submission), GenBank Sequence Database (Accession AF011908), National Center for Biotechnology Information, National Library of Medicine, Bethesda, Maryland, 20894 (GI 2459992; GI 2459993) Oct. 2, 1997.
Klobeck, H.G. et al., (Direct Submission), GenBank Sequence Database (Accession X14810), National Center for Biotechnology Information, National Library of Medicine, Bethesda, Maryland, 20894 (GI 35732; GI 296671) Apr. 29, 1993.
(Direct Submission), GenBank Sequence Database (Accession 130989), National Center for Biotechnology Information, National Library of Medicine, Bethesda, Maryland, 20894 (GI 130989) Jul. 15, 1998.

*Primary Examiner*—Paula K. Hutzell
*Assistant Examiner*—Timothy A Worrall
*Attorney, Agent, or Firm*—Incyte Pharmaceuticals, Inc.

[57] ABSTRACT

The invention provides two human prostate growth-associated membrane proteins (PGAMP) and polynucleotides which identify and encode PGAMP. The invention also provides expression vectors, host cells, antibodies, agonists, and antagonists. The invention also provides methods for diagnosing, treating or preventing disorders associated with expression of PGAMP.

9 Claims, 4 Drawing Sheets

| | | | | | | | |
|---|---|---|---|---|---|---|---|
| 1 | M F L | – | – | – | – | – – – – – – – – – – | 1999442 |
| 214 | D Q L | W V P L R W I A P | E | L V D E V H G N L L V V D Q T K S | GI 2459993 |
| 1 | M W | – | – V P | – | – | V V F L T L S V T W I – – G | GI 130989 |
| | | | | | | | |
| 18 | A A V Y T F T M F F S T F Y H A C D Q P | – | – | – | – – – – – – – G I V | 1999442 |
| 244 | S N W S L G V T I W E L F E L G A Q P Y P Q H S D R Q V L | – | GI 2459993 |
| 17 | A A P L I L – S R I V G G W – E C E K H S | – | – – – – – – – – – – | GI 130989 |
| | | | | | | | |
| 41 | V F C I M D Y D V | – | L Q F C D F L G S L M S V W V T V I A M | 1999442 |
| 274 | A Y A V R E Q Q L K L P K P Q L Q L A L S D R W Y E V M Q F | – | GI 2459993 |
| 36 | – | – | – | – | Q P W Q V L V A | – | GI 130989 |
| | | | | | | | |
| 70 | A R L Q P V V K | – | – | – Q V L | – | Y L L G A M L L S M A | 1999442 |
| 304 | C W L Q P E Q R P T A E E V H L L L S Y L C A K G T T E L E | – | GI 2459993 |
| 44 | S R G R A V C | – | – | – | G G V L V | – | GI 130989 |
| | | | | | | | |
| 92 | L Q L D R H G L W N L L G P S | – | L F A L G I L A T A W T V R | 1999442 |
| 334 | E E F E R R – – W R S L R P G G S T G L G S G S A A P A A A | – | GI 2459993 |
| 56 | – | – | H P Q W V L T A A | – | – – – – – – – – – – | GI 130989 |

FIGURE 2A

```
121  SVRRHCYPPTWRRWLFYLCPGSLIAGSAV           1999442
353  TAASAELTAASSFPLLERFTSDGFHVDSDD          GI 2459993
                                             GI 130989
65   - - - - - IRNKSVILLGRHSL - - FHPE

151  LLYAFVETRDNYFYIHSIWHMLIAGSVGFL          1999442
383  VL - TVTETSHGLNFEYK - WE - - - AGCGAEE  GI 2459993
85   DTGQVFQVSHS - - FPHPLYDMSLLKNR - FL     GI 130989

181  LPPRAKTDHGVPSGARARGCGYQLCINEQE          1999442
418  YPPSGAAS - SPGSAARLQ - - ELCAPDSS       GI 2459993
112  RP - - - - - - - - - - GDDSSHDLMLLRLS   GI 130989

211  EPGPRGPRRGHCQ - - - QHLCQLRGALGLA       1999442
443  PPGVVPVLSAHSPSVGSEYFIRLEGAVPAA          GI 2459993
128  EP - - - - - - - AELTDAVKVMDL - - PTQEP GI 130989

237  LRGYECFLEFFLGVWSPLRRQAVFLEDME           1999442
473  GHDPDCA - - - - - GCAPSPQAVTDQDNN       GI 2459993
147  ALGTTCY - - - ASGWGSIEPEE - - FL - TP   GI 130989
```

PROSTATE GROWTH-ASSOCIATED MEMBRANE PROTEINS

FIELD OF THE INVENTION

This invention relates to nucleic acid and amino acid sequences of two prostate growth-associated membrane proteins and to the use of these sequences in the diagnosis, treatment, and prevention of neoplastic and reproductive disorders.

BACKGROUND OF THE INVENTION

Cancers, or malignant tumors, which are characterized by indefinite cell proliferation and cell death, can be classified into three categories: carcinomas, sarcomas, and leukemia. Recent reports reveal that approximately one in eight women contracts breast cancer, while the risk of prostate cancer is about 9.5% among men over 50 years of age. (Helzlsouer, K. J. (1994) Curr. Opin. Oncol. 6:541–548; Harris, J. R. et al. (1992) N. Engl. J. Med. 327:319–328.) Cancer cells exhibit unique gene expression patterns, and numerous cancer-specific genetic markers, for example, tumor-associated antigens (TAAs), have been identified.

TAAs are surface molecules that are differentially expressed in tumor cells relative to non-tumor tissues. TAAs make tumor cells immunologically distinct from normal cells and provide diagnostic and therapeutic targets for human cancers. (Minegishi, M. et al. (1989) Leukemia Res. 13:43–51, Takagi, S. et al. (1995) Int. J. Cancer 61:706–715.) For example, the discovery of high level expression of the HER2 gene in breast tumors has led to the development of potential therapeutic treatments of breast cancer. (Liu, E. et al. (1992) Oncogene 7:1027–1032; and Kern, J. A. (1993) Am. J. Respir. Cell Mol. Biol. 9:448–454.)

TAAs have been characterized either as membrane proteins or altered carbohydrate moieties in glycoproteins and glycolipids, however the function of TAAs remain largely unknown. One TAA family, the transmembrane 4 superfamily (TM4SF), usually has four well-conserved membrane-spanning regions, certain conserved cysteine residues, and short sequence motifs. There is evidence that TM4SF antigens exist in close association with lymphocyte membrane receptors such as T cells CD4 and CD8 antigens. (Imai, T. and Yoshie, O. (1993) J. Immunol. 151:6470–6481.) Examples of TM4SF antigens include human melanoma-associated antigen ME491, human and mouse leukocyte surface antigen CD37, and human lymphoblastic leukemia-associated TALLA-1. (Hotta, H. et al. (1988) Cancer Res. 48:2955–2962; Classon, B. J. et al. (1989) J. Exp. Med. 169:1497–1502; and Tomlinson, M. G. et al. (1996) Mol. Immun. 33:867–872; Takagi, S. et al. (1995) Int. J. Cancer 61:706–715.)

Adenocarcinoma of the prostate accounts for a significant number of malignancies in men over 50, with over 122,000 new cases occurring each year in the United States alone. Prostate specific antigen (PSA) is a tissue-specific serine protease of the kallikrein family almost exclusively produced by prostatic epithelial cells. Expression of the PSA gene is regulated by androgens. The quantity of PSA correlates with the number and volume of the prostatic epithelial cells. Consequently, the levels of PSA are an excellent indicator of abnormal prostate growth. (Pearson et al. (1994) J. Urol. 152:1743–48.) Careful monitoring of PSA levels over time may provide one tool for detecting prostate cancer. Since PSA is also moderately elevated in patients with benign prostate hyperplasia, additional techniques are needed to distinguish between the two clinical conditions.

Cell and tissue growth is modulated by molecular interactions between growth activators and growth inhibitors. Expression of many growth activating leucine-rich proteins has been shown in developing and proliferating tissue. (Asundi, V. K. and Greher, K. L. (1992) Eur. J. Cell Biol. 59:314–321.) The broad function of the leucine-rich domain is thought to be associated with protein-protein interactions, in particular the leucine zipper motif. (Landschulz, W. H. et al. (1988) Science 240:1759–1764.) In addition, leucine-rich domains have been identified in transcription factor and non-transcription factor proteins. (Vanhaesebroeck, B. et al. (1997) Proc. Natl. Acad. Sci. 94:4330–4335.)

Apoptosis is a genetically controlled process by which unneeded or damaged cells can be eliminated. Apoptosis is initiated by growth inhibitors and by agents that antagonize growth activators. Disregulation of apoptosis has recently been recognized as a significant factor in the pathogenesis of human disease. For example, inappropriate cell survival can cause or contribute to many diseases such as cancer, autoimmune diseases, and inflammatory diseases. (Thompson, C. B. (1995) Science 267:1456–1462.) Proteins which induce apoptosis are termed pro-apoptotic and proteins which prevent apoptosis are termed anti-apoptotic. Anti-apoptotic proteins may contain regions which are homologous to those in pro-apoptotic proteins. (See O'Connor, L. et al. (1998) EMBO J. 17:384–395.)

The discovery of two new prostate growth-associated membrane proteins and the polynucleotides encoding them satisfies a need in the art by providing new compositions which are useful in the diagnosis, treatment, and prevention of neoplastic and reproductive disorders.

SUMMARY OF THE INVENTION

The invention is based on the discovery of two new human prostate growth-associated membrane proteins (PGAMP), the polynucleotides encoding PGAMP, and the use of these compositions for the diagnosis, treatment, or prevention of neoplastic and reproductive disorders.

The invention features substantially purified polypeptides, prostate growth-associated membrane proteins, referred to collectively as "PGAMP" and individually as "PGAMP-1" and "PGAMP-2." In one aspect, the invention provides a substantially purified polypeptide comprising an amino acid sequence selected from the group consisting of SEQ ID NO:1, SEQ ID NO:2, a fragment of SEQ ID NO:1, and a fragment of SEQ ID NO:2.

The invention further provides a substantially purified variant having at least 90% amino acid identity to the amino acid sequences of SEQ ID NO:1 or SEQ ID NO:2, or to a fragment of either of these sequences. The invention also provides an isolated and purified polynucleotide encoding the polypeptide comprising an amino acid sequence selected from the group consisting of SEQ ID NO:1, SEQ ID NO:2, a fragment of SEQ ID NO:1, and a fragment of SEQ ID NO:2. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2, as well as an isolated and purified polynucleotide having a sequence which is complementary to the polynucleotide encoding the polypeptide comprising the amino acid sequence selected from the group consisting of SEQ ID NO:1, SEQ ID NO:2, a fragment of SEQ ID NO:1, and a fragment of SEQ ID NO:2.

The invention also provides an isolated and purified polynucleotide comprising a polynucleotide sequence selected from the group consisting of SEQ ID NO:3, SEQ ID NO:4, a fragment of SEQ ID NO:3, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:3, SEQ ID NO:4, a fragment of SEQ ID NO:3, and a fragment of SEQ ID NO:4, as well as an isolated and purified polynucleotide having a sequence which is complementary to the polynucleotide comprising a polynucleotide sequence selected from the group consisting of SEQ ID NO:3, SEQ ID NO:4, a fragment of SEQ ID NO:3, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2. In another aspect, the expression vector is contained within a host cell.

The invention also provides a method for producing a polypeptide comprising the amino acid sequence selected from the group consisting of SEQ ID NO:1, SEQ ID NO:2, a fragment of SEQ ID NO:1, and a fragment of SEQ ID NO:2, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, a fragment of SEQ ID NO:1, and a fragment of SEQ ID NO:2 in conjunction with a suitable pharmaceutical carrier.

The invention further includes a purified antibody which binds to a polypeptide comprising the amino acid sequence selected from the group consisting of SEQ ID NO:1, SEQ ID NO:2, a fragment of SEQ ID NO:1, and a fragment of SEQ ID NO:2, as well as a purified agonist and a purified antagonist to the polypeptide.

The invention also provides a method for treating or preventing a neoplastic disorder, the method comprising administering to a subject in need of such treatment an effective amount of an antagonist of the polypeptide having an amino acid sequence selected from the group consisting of SEQ ID NO:1, SEQ ID NO:2, a fragment of SEQ ID NO:1, and a fragment of SEQ ID NO:2.

The invention also provides a method for treating or preventing a reproductive disorder, the method comprising administering to a subject in need of such treatment an effective amount of an antagonist of the polypeptide having an amino acid sequence selected from the group consisting of SEQ ID NO:1, SEQ ID NO:2, a fragment of SEQ ID NO:1, and a fragment of SEQ ID NO:2.

The invention also provides a method for detecting a polynucleotide encoding the polypeptide comprising the amino acid sequence selected from the group consisting of SEQ ID NO:1, SEQ ID NO:2, a fragment of SEQ ID NO:1, and a fragment of SEQ ID NO:2 in a biological sample containing nucleic acids, the method comprising the steps of: (a) hybridizing the complement of the polynucleotide sequence encoding the polypeptide comprising the amino acid sequence selected from the group consisting of SEQ ID NO:1. SEQ ID NO:2, a fragment of SEQ ID NO:1, and a fragment of SEQ ID NO:2 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIG. 1 shows the amino acid sequence alignments between PGAMP-1 (1691243; SEQ ID NO:1) and rat heat-stable antigen CD4 (GI 1216498; SEQ ID NO:5), produced using the multisequence alignment program of LASERGENE™ software (DNASTAR Inc, Madison Wis.).

FIGS. 2A, 2B, and 2C show the amino acid sequence alignments among PGAMP-2 (1999442; SEQ ID NO:2), a fragment (D214 to E680) of the mouse apoptosis-associated tyrosine kinase (GI 2459993; SEQ ID NO:6), and human PSA (GI 130989; SEQ ID NO:7), produced using the multisequence alignment program of LASERGENE™ software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions "PGAMP," as used herein, refers to the amino acid sequences of substantially purified PGAMP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to PGAMP, increases or prolongs the duration of the effect of PGAMP. Agonists may include proteins, nucleic acids, carbohydrates, or any other molecules which bind to and modulate the effect of PGAMP.

An "allelic variant," as this term is used herein, is an alternative form of the gene encoding PGAMP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding PGAMP, as described herein, include those sequences with deletions, insertions, or substitutions of different nucleotides, resulting in a polynucleotide the same as PGAMP or a polypeptide with at least one functional characteristic of PGAMP. Included within this definition are polymorphisms which may or may not be readily detectable using a particular oligonucleotide probe of the polynucleotide encoding PGAMP, and improper or unexpected hybridization to allelic variants, with a locus other than the normal chromosomal locus for the polynucleotide sequence encoding PGAMP. The encoded protein may also be "altered," and may contain deletions, insertions, or substitutions of amino acid residues which produce a silent change and result in a functionally equivalent PGAMP. Deliberate amino acid substitutions may be made on the basis of similarity in polarity, charge, solubility, hydrophobicity, hydrophilicity, and/or the amphipathic nature of the residues, as long as the biological or immunological activity of PGAMP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of PGAMP which are preferably about 5 to about 15 amino acids in length, most preferably 14 amino acids, and which retain some biological activity or immunological activity of PGAMP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) PCR Primer, a Laboratory Manual, Cold Spring Harbor Press, Plainview, N.Y., pp.1–5.)

The term "antagonist," as it is used herein, refers to a molecule which, when bound to PGAMP, decreases the amount or the duration of the effect of the biological or immunological activity of PGAMP. Antagonists may include proteins, nucleic acids, carbohydrates, antibodies, or any other molecules which decrease the effect of PGAMP.

As used herein, the term "antibody" refers to intact molecules as well as to fragments thereof, such as Fab, F(ab')$_2$, and Fv fragments, which are capable of binding the epitopic determinant. Antibodies that bind PGAMP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic PGAMP, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding PGAMP or fragments of PGAMP may be employed as hybridization probes. The probes may be stored in freezedried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding PGAMP, by Northern analysis is indicative of the presence of nucleic acids encoding PGAMP in a sample, and thereby correlates with expression of the transcript from the polynucleotide encoding PGAMP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of PGAMP. For example, modulation may cause an increase or a decrease in protein activity, binding characteristics, or any other biological, functional, or immunological properties of PGAMP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding PGAMP, or fragments thereof, or PGAMP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of PGAMP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The Invention

The invention is based on the discovery of new human prostate growth-associated membrane proteins (PGAMP), the polynucleotides encoding PGAMP, and the use of these compositions for the diagnosis, treatment, or prevention of neoplastic and reproductive disorders.

Nucleic acids encoding the PGAMP-1 of the present invention were first identified in Incyte Clone 1691243 from the prostate cDNA library (PROSTUT10) using a computer search, e.g., BLAST, for amino acid sequence alignments. A consensus sequence, SEQ ID NO:3, was derived from the following overlapping and/or extended nucleic acid sequences: Incyte Clones 1691243H1 (PROSTUT10), 899754H1 (BRSTTUT03), 2796994F6 (NPOLNOT01), and the shotgun sequences SBAA03738F1 and SBAA02693F1.

In one embodiment, the invention encompasses a polypeptide comprising the amino acid sequence of SEQ ID NO:1. As shown in FIG. 1, PGAMP-1 is 141 amino acids in length and has one potential casein kinase II phosphorylation site at residue S35; one potential protein kinase C phosphorylation site at residue S15; one potential tyrosine kinase phosphorylation site at residue Y110; three potential transmembrane regions between about residues 144 to P67, I81 to W102, and P117 to Q135; and has chemical similarity with CD44 antigen precursor. In addition, as shown in FIG. 1, PGAMP-1 has chemical and structural similarity with rat heat-stable antigen CD4 (GI 1216498; SEQ ID NO:5). In particular, PGAMP-1 and rat heat-stable antigen CD4 share 21% identity and two potential transmembrane domains. A fragment of SEQ ID NO:3 from about nucleotide 470 to about nucleotide 493 is useful, for example, for designing oligonucleotides or as a hybridization probe. Northern analysis shows the expression of this sequence in various libraries, at least 72% of which are immortalized or cancerous and at least 18% of which involve immune response. Of particular note is the expression of PGAMP in cancerous or hyperplastic prostate (48%) and breast (7%); and in brain and adrenal gland.

Nucleic acids encoding the PGAMP-2 of the present invention were first identified in Incyte Clone 1999442 from the breast cDNA library (BRSTTUT03) using a computer search, e.g., BLAST, for amino acid sequence alignments. A consensus sequence, SEQ ID NO:4, was derived from the following overlapping and/or extended nucleic acid sequences: Incyte Clones 1999442H1 (BRSTTUT03), 2602378T6 (UTRSNOT10), 12129845R3 (BRSTTUT01), 1636580F6 (UTRSNOT06), and 1857026T6 (PROSNOT18).

Figure 2C:
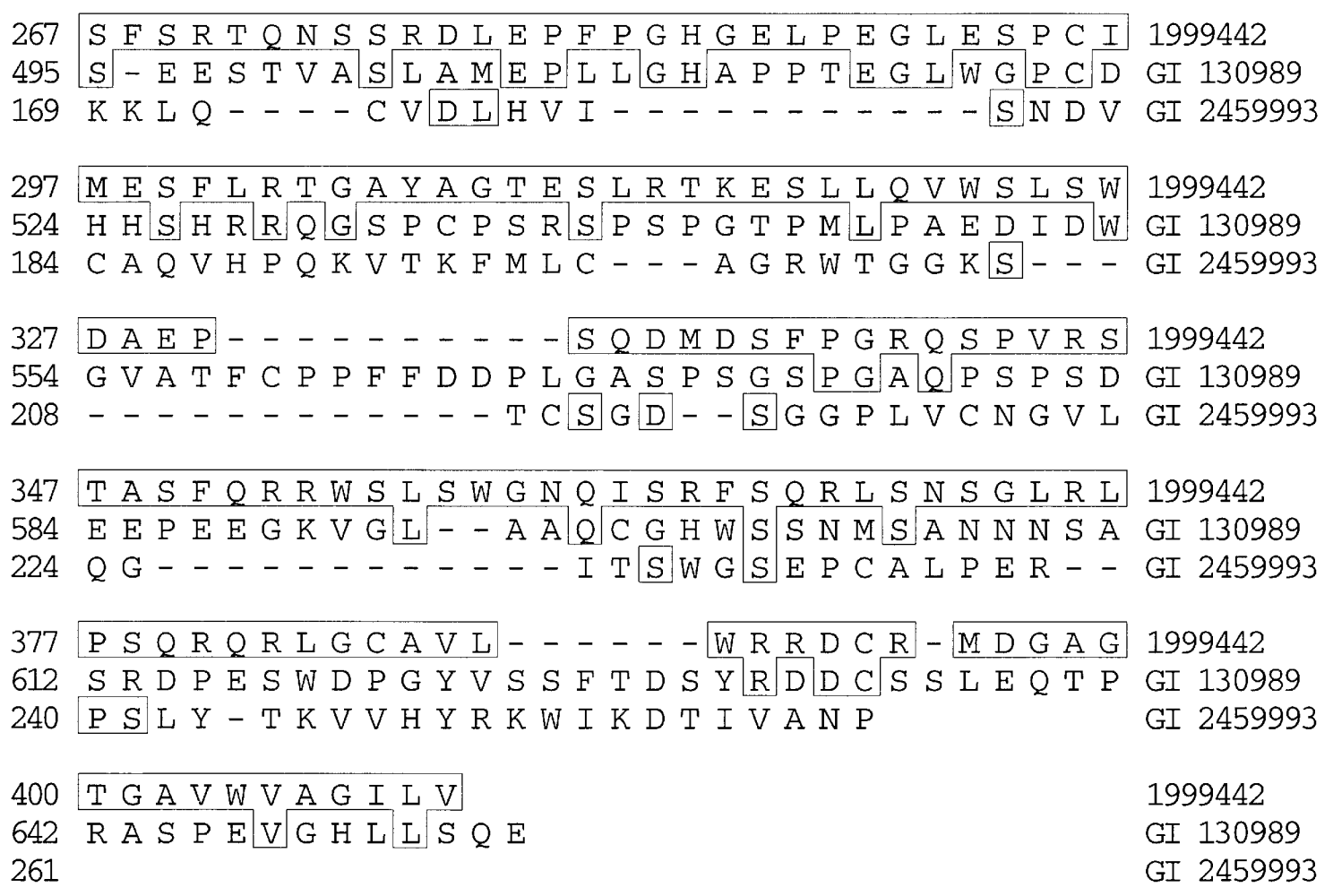

In one embodiment, the invention encompasses a polypeptide comprising the amino acid sequence of SEQ ID NO:2. As shown in FIGS. 2A, 2B, and 2C, PGAMP-2 is 410 amino acids in length and has a potential N-glycosylation site at residue N273; one potential cAMP- and cGMP-dependent protein kinase phosphorylation site at residue S355; one potential casein kinase II phosphorylation site at residue S274; seven potential protein kinase C phosphorylation sites at residues T118, S121, T131, S274, S311, S366, and S378; one potential tyrosine kinase phosphorylation site at residue Y21. In addition, a hydropathy plot of PGAMP-2 predicts nine potential transmembrane regions between about residues L16 to Y31, P37 to V49, Q51 to Q73, V76 to L92, N101 to T118, F137 to F155, I165 to P182, R230 to W251, and T400 to V410; and a potential signal peptide sequence from M1 to S12. As shown in FIGS. 2A, 2B, and 2C, PGAMP-2 has chemical and structural similarity with a fragment (D214 to E680) of the mouse apoptosis-associated tyrosine kinase (GI 2459993; SEQ ID NO:6) and human PSA (GI 130989; SEQ ID NO:7). In particular, PGAMP-2 shares 17% and 18% identity with the fragment (D214 to E680) of the mouse apoptosis-associated tyrosine kinase and human PSA, respectively. The three proteins also share six potential transmembrane regions and the potential signal peptide. In addition, PGAMP-2 and human PSA have rather similar isoelectric points, 8.7 and 7.5, respectively. A fragment of SEQ ID NO:4 from about nucleotide 34 to about nucleotide 51 is useful, for example, for designing oligonucleotides or as a hybridization probe. Northern analysis shows the expression of this sequence in various libraries, at least 76% of which are immortalized or cancerous and at least 18% of which involve immune response. Of particular note is the expression of PGAMP-2 in cancerous or hyperplastic prostate (28%) and breast (10%); and in uterus, ovary, and colon.

The invention also encompasses PGAMP variants. A preferred PGAMP variant is one which has at least about 80%, more preferably at least about 90%, and most preferably at least about 95% amino acid sequence identity to the PGAMP amino acid sequence, and which contains at least one functional or structural characteristic of PGAMP.

The invention also encompasses polynucleotides which encode PGAMP. In a particular embodiment, the invention encompasses a polynucleotide sequence comprising the sequence of SEQ ID NO:3, which encodes a PGAMP. In a further embodiment, the invention encompasses the polynucleotide sequence comprising the sequence of SEQ ID NO:4, which encodes a PGAMP.

The invention also encompasses a variant of a polynucleotide sequence encoding PGAMP. In particular, such a variant polynucleotide sequence will have at least about 80%, more preferably at least about 90%, and most preferably at least about 95% polynucleotide sequence identity to the polynucleotide sequence encoding PGAMP. A particular aspect of the invention encompasses a variant of SEQ ID NO:3 which has at least about 80%, more preferably at least about 90%, and most preferably at least about 95% polynucleotide sequence identity to SEQ ID NO:3. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of PGAMP.

It will be appreciated by those skilled in the art that as a result of the degeneracy of the genetic code, a multitude of polynucleotide sequences encoding PGAMP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PGAMP, and all such variations are to be considered as being specifically disclosed.

Although nucleotide sequences which encode PGAMP and its variants are preferably capable of hybridizing to the nucleotide sequence of the naturally occurring PGAMP under appropriately selected conditions of stringency, it may be advantageous to produce nucleotide sequences encoding PGAMP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PGAMP and its derivatives without altering the encoded amino acid sequences include the production of RNA transcripts having more desirable properties, such as a greater half-life, than transcripts produced from the naturally occurring sequence.

The invention also encompasses production of DNA sequences which encode PGAMP and PGAMP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding PGAMP or any fragment thereof.

Also encompassed by the invention are polynucleotide sequences that are capable of hybridizing to the claimed polynucleotide sequences, and, in particular, to those shown in SEQ ID NO:3, SEQ ID NO:4, a fragment of SEQ ID NO:3, or a fragment of SEQ ID NO:4, under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 μg/ml ssDNA. Useful variations on these conditions will be readily apparent to those skilled in the art.

The washing steps which follow hybridization can also vary in stringency. Wash to stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known and generally available in the art and may be used to practice any of the embodiments of the invention. The methods may employ such enzymes as the Klenow fragment of DNA polymerase I, Sequenase® (U.S. Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding PGAMP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode PGAMP may be cloned in recombinant DNA molecules that direct expression of PGAMP, or fragments or functional equivalents thereof, in appropriate host cells. Due to the inherent degeneracy of the genetic code, other DNA sequences which encode substantially the same or a functionally equivalent amino acid sequence may be produced and used to express PGAMP.

The nucleotide sequences of the present invention can be engineered using methods generally known in the art in order to alter PGAMP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding PGAMP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, PGAMP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of PGAMP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active PGAMP, the nucleotide sequences encoding PGAMP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding PGAMP. Such elements may vary in their strength and specificity. Specific initiation signals may also be used to achieve more efficient translation of sequences encoding PGAMP. Such signals include the ATG initiation codon and adjacent sequences, e.g. the Kozak sequence. In cases where sequences encoding PGAMP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding PGAMP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding PGAMP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding PGAMP. For example, routine cloning, subcloning, and propagation of polynucleotide sequences encoding PGAMP can be achieved using a multifunctional *E. coli* vector such as Bluescript® (Stratagene) or pSport1™ plasmid (GIBCO BRL). Ligation of sequences encoding PGAMP into the vector's multiple cloning site disrupts the lacZ gene, allowing a calorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of PGAMP are needed, e.g. for the production of antibodies, vectors which direct high level expression of PGAMP may be used. For example, vectors containing the strong, inducible T5 or T7 bacteriophage promoter may be used.

Yeast expression systems may be used for production of PGAMP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of PGAMP. Transcription of sequences encoding PGAMP may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding PGAMP may be ligated into an adenovirus transcription/translation complex consisting of the late promoter and tripartite leader sequence. Insertion in a non-essential E1 or E3 region of the viral genome may be used to obtain infective virus which expresses PGAMP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of PGAMP in cell lines is preferred. For example, sequences encoding PGAMP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) antibiotic, or herbic antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate B-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding PGAMP is inserted within a marker gene sequence, transformed cells containing sequences encoding PGAMP can be identified by the absence of marker gene function. Alternatively, a marker gene can be placed in tandem with a sequence encoding PGAMP under the control of a single promoter. Expression of the marker gene in response to induction or selection usually indicates expression of the tandem gene as well.

In general, host cells that contain the nucleic acid sequence encoding PGAMP and that express PGAMP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of PGAMP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PGAMP is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PGAMP include oligolabeling, nick translation, end-labeling, or PCR amplification using a labeled nucleotide. Alternatively, the sequences encoding PGAMP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Minn.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding PGAMP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode PGAMP may be designed to contain signal sequences which direct secretion of PGAMP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding PGAMP may be ligated to a heterologous sequence resulting in translation of a fusion protein in any of the aforementioned host systems. For example, a chimeric PGAMP protein containing a heterologous moiety that can be recognized by a commercially available antibody may facilitate the screening of peptide libraries for inhibitors of PGAMP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the PGAMP encoding sequence and the heterologous protein sequence, so that PGAMP may be cleaved away from the heterologous moiety following purification. Methods for fusion protein expression and purification are discussed in Ausubel, F. M. et al. (1995 and periodic supplements) *Current Protocols in Molecular Biology,* John Wiley & Sons, New York, N.Y., ch 10. A variety of commercially available kits may also be used to facilitate expression and purification of fusion proteins.

In a further embodiment of the invention, synthesis of radiolabeled PGAMP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of PGAMP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431 A Peptide Synthesizer (Perkin Elmer). Various fragments of PGAMP may be synthesized separately and then combined to produce the full length molecule.

Therapeutics

Chemical and structural similarity exists between PGAMP-1 and rat heat-stable antigen CD4 (GI 1216498). In addition, PGAMP-1 is expressed in cancerous or hyperplastic prostate (48%) and breast (7%); and in brain and adrenal gland. Therefore, PGAMP-1 appears to play a role in neoplastic and reproductive disorders.

Chemical and structural similarity exists among PGAMP-2 and a fragment (D214 to E680) of the mouse apoptosis-associated tyrosine kinase (GI 2459993), and human PSA (GI 130989). In addition, PGAMP-2 is expressed in cancerous or hyperplastic prostate (28%) and breast (10%); and in uterus, ovary, and colon. Therefore, PGAMP-2 appears to play a role in neoplastic and reproductive disorders.

Therefore, in one embodiment, an antagonist of PGAMP may be administered to a subject to treat or prevent a neoplastic disorder. Such a neoplastic disorder may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PGAMP may be used directly as an antagonist or indirectly as a targeting or delivery mechanism for bringing a pharmaceutical agent to cells or tissue which express PGAMP.

In an additional embodiment, a vector expressing the complement of the polynucleotide encoding PGAMP may be administered to a subject to treat or prevent a neoplastic disorder including, but not limited to, those described above.

In one embodiment, an antagonist of PGAMP may be administered to a subject to treat or prevent a reproductive disorder. Such a reproductive disorder may include, but is not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. In one aspect, an antibody which specifically binds PGAMP may be used directly as an antagonist or indirectly as a targeting or delivery mechanism for bringing a pharmaceutical agent to cells or tissue which express PGAMP.

In an additional embodiment, a vector expressing the complement of the polynucleotide encoding PGAMP may be administered to a subject to treat or prevent a reproductive disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PGAMP may be produced using methods which are generally known in the art. In particular, purified PGAMP may be used to produce antibodies or to screen libraries of pharmaceutical agents to identify those which specifically bind PGAMP. Antibodies to PGAMP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with PGAMP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PGAMP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of PGAMP amino acids may be fused with those of another protein, such as KLH, and antibodies to the chimeric molecule may be produced.

Monoclonal antibodies to PGAMP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mot. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L,. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PGAMP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; and Winter, G. et al. (1991) Nature 349:293–299.)

Antibody fragments which contain specific binding sites for PGAMP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PGAMP and its specific antibody. A two-site, monoclonal-based immunoassay utilizing monoclonal antibodies reactive to two non-interfering PGAMP epitopes is preferred, but a competitive binding assay may also be employed. (Maddox, supra.)

In another embodiment of the invention, the polynucleotides encoding PGAMP, or any fragment or complement thereof, may be used for therapeutic purposes. In one aspect, the complement of the polynucleotide encoding PGAMP may be used in situations in which it would be desirable to block the transcription of the mRNA. In particular, cells may be transformed with sequences complementary to polynucleotides encoding PGAMP. Thus, complementary molecules or fragments may be used to modulate PGAMP activity, or to achieve regulation of gene function. Such technology is now well known in the art, and sense or antisense oligonucleotides or larger fragments can be designed from various locations along the coding or control regions of sequences encoding PGAMP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding PGAMP. (See, e.g., Sambrook, supra; and Ausubel, supra.) Genes encoding PGAMP can be turned off by transforming a cell or tissue with expression vectors which express high levels of a polynucleotide, or fragment thereof, encoding PGAMP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding PGAMP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PGAMP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PGAMP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of PGAMP, antibodies to PGAMP, and mimetics, agonists, antagonists, or inhibitors of PGAMP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following:1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of PGAMP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example PGAMP or fragments thereof, antibodies of PGAMP, and agonists, antagonists or inhibitors of PGAMP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PGAMP may be used for the diagnosis of disorders characterized by expression of PGAMP, or in assays to monitor patients being treated with PGAMP or agonists, antagonists, or inhibitors of PGAMP. Antibodies useful for diagnostic purposes may be prepared in the same manner as described above for therapeutics. Diagnostic assays for PGAMP include methods which utilize the antibody and a label to detect PGAMP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PGAMP, including ELISAs, RIAs, and FACS, are known in the art and provide a basis for diagnosing altered or abnormal levels of PGAMP expression. Normal or standard values for PGAMP expression are established by combining body fluids or cell extracts taken from normal mammalian subjects, preferably human, with antibody to PGAMP under conditions suitable for complex formation The amount of standard complex formation may be quantitated by various methods, preferably by photometric means. Quantities of PGAMP expressed in subject, control, and disease samples from biopsied tissues are compared with the standard values. Deviation between standard and subject values establishes the parameters for diagnosing disease.

In another embodiment of the invention, the polynucleotides encoding PGAMP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PGAMP may be correlated with disease. The diagnostic assay may be used to determine absence, presence, and excess expression of PGAMP, and to monitor regulation of PGAMP levels during therapeutic intervention.

In one aspect, hybridization with PCR probes which are capable of detecting polynucleotide sequences, including genomic sequences, encoding PGAMP or closely related molecules may be used to identify nucleic acid sequences which encode PGAMP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding PGAMP, allelic variants, or related sequences.

Probes may also be used for the detection of related sequences, and should preferably have at least 50% sequence identity to any of the PGAMP encoding sequences. The hybridization probes of the subject invention may be DNA or RNA and may be derived from the sequences of SEQ ID NO:2, SEQ ID NO:4, or from genomic sequences including promoters, enhancers, and introns of the PGAMP gene.

Means for producing specific hybridization probes for DNAs encoding PGAMP include the cloning of polynucleotide sequences encoding PGAMP or PGAMP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding PGAMP may be used for the diagnosis of a disorder associated with expression of PGAMP. Examples of such a disorder include, but are not limited to, a neoplastic disorder, such as, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and a reproductive disorder, such as, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. The polynucleotide sequences encoding PGAMP may be used in Southern or Northern analysis, dot blot, or other membrane-based technologies; in PCR technologies; in dipstick, pin, and ELISA assays; and in microarrays utilizing fluids or tissues from patients to detect altered PGAMP expression. Such qualitative or quantitative methods are well known in the art.

In a particular aspect, the nucleotide sequences encoding PGAMP may be useful in assays that detect the presence of associated disorders, particularly those mentioned above. The nucleotide sequences encoding PGAMP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding PGAMP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PGAMP, a normal or standard profile for expression is established. This may be accomplished by combining body fluids or cell extracts taken from normal subjects, either animal or human, with a sequence, or a fragment thereof, encoding PGAMP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PGAMP may involve the use of PCR. These oligomers may be chemically synthesized, generated enzymatically, or produced in vitro. Oligomers will preferably contain a fragment of a polynucleotide encoding PGAMP, or a fragment of a polynucleotide complementary to the polynucleotide encoding PGAMP, and will be employed under optimized conditions for identification of a specific gene or condition. Oligomers may also be employed under less stringent conditions for detection or quantitation of closely related DNA or RNA sequences.

Methods which may also be used to quantitate the expression of PGAMP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding PGAMP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp. 965–968.) Examples of genetic map data can be found in various scientific journals or at the Online Mendelian Inheritance in Man (OMIM) site. Correlation between the location of the gene encoding PGAMP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, PGAMP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PGAMP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with PGAMP, or fragments thereof, and washed. Bound PGAMP is then detected by methods well known in the art. Purified PGAMP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PGAMP specifically compete with a test compound for binding PGAMP. In this manner, antibodies can be used to detect the presence of any peptide which shares one or more antigenic determinants with PGAMP.

In additional embodiments, the nucleotide sequences which encode PGAMP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

PROSTUT10

The PROSTUT10 library was constructed using polyA RNA isolated from prostatic tumor tissue removed from a 66-year-old Caucasian male during radical prostatectomy and regional lymph node excision. Pathology indicated an adenocarcinoma (Gleason grade 2+3) in the left and right side centrally. Adenofibromatous hyperplasia was also present. The patient presented with elevated prostate specific antigen (PSA). Family history included prostate cancer, secondary bone cancer, and benign hypertension. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

BRSTTUT03

The BRSTTUT03 library was constructed using polyA RNA isolated from breast tumor tissue removed from a 58-year-old Caucasian female during a unilateral extended simple mastectomy. Pathology indicated multicentric invasive grade 4 lobular carcinoma. Patient history included skin cancer, rheumatic heart disease, osteoarthritis, and tuberculosis. Patient medications included tamoxifen to inhibit the induction of mammary carcinoma. Family history included cerebrovascular disease, coronary artery aneurysm, breast cancer; prostate cancer; cerebrovascular disease, atherosclerotic coronary artery disease, and Type I diabetes. cDNA synthesis was initiated using a NotI-oligo(dT) primer. Double-stranded cDNA was blunted, ligated to SaI adaptors, digested with NotI, size-selected, and cloned into the NotI and SaI sites of the pSPORT1 vector.

II. Isolation and Sequencing of cDNA Clones

For both libraries, plasmid DNA was released from the cells and purified using the REAL Prep 96 plasmid kit (Catalog #26173, QIAGEN, Inc.). The recommended protocol was employed except for the following changes:1) the bacteria were cultured in 1 ml of sterile Terrific Broth (Catalog #22711, GIBCO-BRL) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and 10–8 for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. And Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results:75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding PGAMP occurs. Abundance and percent abundance are also reported. Abundance directly reflects the number of times a particular transcript is represented in a cDNA library, and percent abundance is abundance divided by the total number of sequences examined in the cDNA library.

V. Extension of PGAMP Encoding Polynucleotides

The nucleic acid sequences of Incyte Clones 1691243 and 1999442 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4 through 6 for an additional 15 cycles
Step 8 94° C. for 15 sec
Step 9 65° C. for 1 min
Step 10 68° C. for 7:15 min
Step 11 Repeat steps 8 through 10 for an additional 12 cycles
Step 12 72° C. for 8 min
Step 13 4° C. (and holding)

A 5 $\mu$l to 10 $\mu$l aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 $\mu$l of ligation buffer, 1 $\mu$l T4-DNA ligase (15 units) and 1 $\mu$l T4 polynucleotide kinase were added, and the mixture was incubated at room temperature for 2 to 3 hours, or overnight at 16° C. Competent E. coli cells (in 40 $\mu$l of appropriate media) were transformed with 3 $\mu$l of ligation mixture and cultured in 80 $\mu$l of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 $\mu$l of liquid LB/2× carb medium placed in an individual well of an appropriate commercially-available sterile 96-well microtiter plate. The following day, 5 $\mu$l of each overnight culture was transferred into a non-sterile 96-well plate and, after dilution 1:10 with water, 5 $\mu$l from each sample was transferred into a PCR array.

For PCR amplification, 18 $\mu$l of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2 through 4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:3 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 $\mu$Ci of $[\gamma\text{-}^{32}P]$ adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, BglI, Eco RI, Pst I, Xba1, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the PGAMP-encoding sequences, or any parts thereof, are used to detect, decrease, or inhibit expression of naturally occurring PGAMP. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of PGAMP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PGAMP-encoding transcript.

IX. Expression of PGAMP

Expression and purification of PGAMP is achieved using bacterial or virus-based expression systems. For expression of PGAMP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express PGAMP upon induction with isopropyl beta-D-thiogalactopyranoside (IPTG). Expression of PGAMP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding PGAMP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. U.S.A. 91:3224–3227; Sandig, V. et al. (1996) Hum. Gene Ther. 7:1937–1945.)

In most expression systems, PGAMP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from PGAMP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified PGAMP obtained by these methods can be used directly in the following activity assay.

X. Demonstration of PGAMP Activity

PGAMP activity can be measured by stimulation of cell growth of cell lines or tissues transformed with a vector containing PGAMP. Transformed and control cells are seeded and cultured in chemically defined serum-free medium. An antibody for PGAMP is added 18 hours after seeding. After 24 hours, cultures are pulse-labeled for 18 hours with 1 $\mu$Ci of [methyl-$^3$H]thymidine. Cells are treated with trypsin and collected with an automatic cell harvester. Cell-associated radioactivity is determined in triplicate by liquid scintillation counting.

XI. Functional Assays

PGAMP function is assessed by expressing the sequences encoding PGAMP at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of PGAMP on gene expression can be assessed using highly purified populations of cells transfected with sequences encoding PGAMP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding PGAMP and other genes of interest can be analyzed by Northern analysis or microarray techniques.

XII. Production of PGAMP Specific Antibodies

PGAMP substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the PGAMP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431 A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring PGAMP Using Specific Antibodies

Naturally occurring or recombinant PGAMP is substantially purified by immunoaffinity chromatography using antibodies specific for PGAMP. An immunoaffinity column is constructed by covalently coupling anti-PGAMP antibody to an activated chromatographic resin, such as CNBr-activated Sepharose (Pharmacia & Upjohn). After the coupling, the resin is blocked and washed according to the manufacturer's instructions.

Media containing PGAMP are passed over the immunoaffinity column, and the column is washed under conditions that allow the preferential absorbance of PGAMP (e.g., high ionic strength buffers in the presence of detergent). The column is eluted under conditions that disrupt antibody/PGAMP binding (e.g., a buffer of pH 2 to pH 3, or a high concentration of a chaotrope, such as urea or thiocyanate ion), and PGAMP is collected.

XIV. Identification of Molecules Which Interact with PGAMP

PGAMP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled PGAMP, washed, and any wells with labeled PGAMP complex are assayed. Data obtained using different concentrations of PGAMP are used to calculate values for the number, affinity, and association of PGAMP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide encoding a polypeptide comprising an amino acid sequence selected from the group consisting of SEQ ID NO:1 and SEQ ID NO:2.

2. An isolated and purified polynucleotide which is fully complementary to the polynucleotide of claim 3.

3. An isolated and purified polynucleotide comprising a polynucleotide sequence selected from the group consisting of SEQ ID NO:3 and SEQ ID NO:4.

4. An isolated and purified polynucleotide having a sequence that is fully complementary to the polynucleotide of claim 3.

5. An expression vector comprising the polynucleotide of claim 3.

6. A host cell comprising the expression vector of claim 5.

7. A method for producing a polypeptide comprising the amino acid sequence selected from the group consisting of SEQ ID NO:1 and SEQ ID NO:2, the method comprising the steps of:
   (a) culturing the host cell of claim 6 under conditions suitable for the expression of the polypeptide; and
   (b) recovering the polypeptide from the host cell culture.

8. A method for detecting a polynucleotide encoding the polypeptide comprising the amino acid sequence selected from the group consisting of SEQ ID NO:1 and SEQ ID NO:2 in a sample containing nucleic acids, the method comprising the steps of:
   (a) hybridizing the polynucleotide of claim 6 to at least one of the nucleic acids of the sample, thereby forming a hybridization complex; and
   (b) detecting the hybridization complex, wherein the presence of the hybridization complex correlates with the presence of a polynucleotide encoding the polypeptide in the sample.

9. The method of claim 8 wherein the nucleic acids of the biological sample are amplified by the polymerase chain reaction prior to the hybridizing step.

* * * * *

UNITED STATES PATENT AND TRADEMARK OFFICE
CERTIFICATE OF CORRECTION

PATENT NO. : 6,048,970
DATED : April 11, 2000
INVENTOR(S) : Lal et al.

It is certified that error appears in the above-identified patent and that said Letters Patent is hereby corrected as shown below:

Column 53,
Line 66, please replace "An isolated and purified polynucleotide which is fully complementary to the polynucleotide of claim 3." with
-- An isolated and purified polynucleotide which is fully complementary to the polynucleotide of claim 1. --

Column 54,
Line 1, please replace "An expression vector comprising the polynucleotide of claim 3." with -- An expression vector comprising the polynucleotide of claim 1. --

Signed and Sealed this

Seventh Day of October, 2003

JAMES E. ROGAN
*Director of the United States Patent and Trademark Office*

SEQUENCE LISTING (1) GENERAL INFORMATION:

(iii) NUMBER OF SEQUENCES: 7

(2) INFORMATION FOR SEQ ID NO:    1:

(i) SEQUENCE CHARACTERISTICS:
        (A) LENGTH: 141 amino acids
        (B) TYPE: amino acid
        (C) STRANDEDNESS: single
        (D) TOPOLOGY: linear (vii) IMMEDIATE SOURCE:
        (A) LIBRARY: PROSTUT10
        (B) CLONE: 1691243

(xi) SEQUENCE DESCRIPTION: SEQ ID NO: 1 :

```
Met Val His Val Ala Tyr Ser Leu Cys Leu Pro Met Arg Arg Ser
                  5                  10                  15

Glu Arg Tyr Leu Phe Leu Asn Met Ala Tyr Gln Gln Val His Ala
                 20                  25                  30
```

```
Asn Ile Glu Asn Ser Trp Asn Glu Glu Val Trp Arg Ile Glu
                35                  40                  45

Met Tyr Ile Ser Phe Gly Ile Met Ser Leu Gly Leu Leu Ser Leu
                50                  55                  60

Leu Ala Val Thr Ser Ile Pro Ser Val Ser Asn Ala Leu Asn Trp
                65                  70                  75

Arg Glu Phe Ser Phe Ile Gln Ser Thr Leu Gly Tyr Val Ala Leu
                80                  85                  90

Leu Ile Ser Thr Phe His Val Leu Ile Tyr Gly Trp Lys Arg Ala
                95                 100                 105

Phe Glu Glu Glu Tyr Tyr Arg Phe Tyr Thr Pro Pro Asn Phe Val
               110                 115                 120

Leu Ala Leu Val Leu Pro Ser Ile Val Ile Leu Asp Leu Leu Gln
               125                 130                 135

Leu Cys Arg Tyr Pro Asp
               140
```

(2) INFORMATION FOR SEQ ID NO:    2:

(i) SEQUENCE CHARACTERISTICS:
        (A) LENGTH: 410 amino acids
        (B) TYPE: amino acid
        (C) STRANDEDNESS: single
        (D) TOPOLOGY: linear (vii) IMMEDIATE SOURCE:
        (A) LIBRARY: BRSTTUT03
        (B) CLONE: 1999442

(xi) SEQUENCE DESCRIPTION: SEQ ID NO: 2 :

```
Met Phe Leu Pro Pro Val Val Leu Ala Ile Arg Ser Arg Tyr Val
                 5                  10                  15

Leu Glu Ala Ala Val Tyr Thr Phe Thr Met Phe Phe Ser Thr Phe
                20                  25                  30

Tyr His Ala Cys Asp Gln Pro Gly Ile Val Val Phe Cys Ile Met
                35                  40                  45

Asp Tyr Asp Val Leu Gln Phe Cys Asp Phe Leu Gly Ser Leu Met
                50                  55                  60

Ser Val Trp Val Thr Val Ile Ala Met Ala Arg Leu Gln Pro Val
                65                  70                  75

Val Lys Gln Val Leu Tyr Leu Leu Gly Ala Met Leu Leu Ser Met
                80                  85                  90

Ala Leu Gln Leu Asp Arg His Gly Leu Trp Asn Leu Leu Gly Pro
                95                 100                 105

Ser Leu Phe Ala Leu Gly Ile Leu Ala Thr Ala Trp Thr Val Arg
               110                 115                 120

Ser Val Arg Arg Arg His Cys Tyr Pro Pro Thr Trp Arg Arg Trp
               125                 130                 135

Leu Phe Tyr Leu Cys Pro Gly Ser Leu Ile Ala Gly Ser Ala Val
               140                 145                 150

Leu Leu Tyr Ala Phe Val Glu Thr Arg Asp Asn Tyr Phe Tyr Ile
               155                 160                 165

His Ser Ile Trp His Met Leu Ile Ala Gly Ser Val Gly Phe Leu
               170                 175                 180

Leu Pro Pro Arg Ala Lys Thr Asp His Gly Val Pro Ser Gly Ala
               185                 190                 195
```

```
Arg Ala Arg Gly Cys Gly Tyr Gln Leu Cys Ile Asn Glu Gln Glu
                200                 205                 210

Glu Pro Gly Pro Arg Gly Pro Arg Arg Gly His Cys Gln Gln His
                215                 220                 225

Leu Cys Gln Leu Arg Gly Ala Leu Gly Leu Ala Leu Arg Gly Tyr
                230                 235                 240

Glu Cys Phe Leu Glu Phe Phe Leu Gly Val Trp Ser Pro Leu Arg
                245                 250                 255

Arg Arg Gln Ala Val Phe Leu Glu Asp Met Glu Ser Phe Ser Arg
                260                 265                 270

Thr Gln Asn Ser Ser Arg Asp Leu Glu Pro Phe Pro Gly His Gly
                275                 280                 285

Glu Leu Pro Glu Gly Leu Glu Ser Pro Cys Ile Met Glu Ser Phe
                290                 295                 300

Leu Arg Thr Gly Ala Tyr Ala Gly Thr Glu Ser Leu Arg Thr Lys
                305                 310                 315

Glu Ser Leu Leu Gln Val Trp Ser Leu Ser Trp Asp Ala Glu Pro
                320                 325                 330

Ser Gln Asp Met Asp Ser Phe Pro Gly Arg Gln Ser Pro Val Arg
                335                 340                 345

Ser Thr Ala Ser Phe Gln Arg Arg Trp Ser Leu Ser Trp Gly Asn
                350                 355                 360

Gln Ile Ser Arg Phe Ser Gln Arg Leu Ser Asn Ser Gly Leu Arg
                365                 370                 375

Leu Pro Ser Gln Arg Gln Arg Leu Gly Cys Ala Val Leu Trp Arg
                380                 385                 390

Arg Asp Cys Arg Met Asp Gly Ala Gly Thr Gly Ala Val Trp Val
                395                 400                 405

Ala Gly Ile Leu Val
                410

(2) INFORMATION FOR SEQ ID NO:    3:

(i) SEQUENCE CHARACTERISTICS:
        (A) LENGTH: 1213 base pairs
        (B) TYPE: nucleic acid
        (C) STRANDEDNESS: single
        (D) TOPOLOGY: linear (vii) IMMEDIATE SOURCE:
        (A) LIBRARY: PROSTUT10
        (B) CLONE: 1691243

(xi) SEQUENCE DESCRIPTION: SEQ ID NO: 3 :

CAAGTATAGG AGATTTCCAC CTTGGTTGGA AACCTGGTTA CAGTGTAGAA AACAGCTTGG      60

ATTACTAAGT TTTTTCTTCG CTATGGTCCA TGTTGCCTAC AGCCTCTGCT TACCGATGAG     120

AAGGTCAGAG AGATATTTGT TTCTCAACAT GGCTTATCAG CAGGTTCATG CAAATATTGA     180

AAACTCTTGG AATGAGGAAG AAGTTTGGAG AATTGAAATG TATATCTCCT TTGGCATAAT     240

GAGCCTTGGC TTACTTTCCC TCCTGGCAGT CACTTCTATC CCTTCAGTGA GCAATGCTTT     300

AAACTGGAGA GAATTCAGTT TTATTCAGTC TACACTTGGA TATGTCGCTC TGCTCATAAG     360

TACTTTCCAT GTTTTAATTT ATGGATGGAA ACGAGCTTTT GAGGAAGAGT ACTACAGATT     420

TTATACACCA CCAAACTTTG TTCTTGCTCT TGTTTTGCCC TCAATTGTAA TTCTGGATCT     480

TTTGCAGCTT TGCAGATACC CAGACTGAGC TGGAACTGGA ATTTGTCTTC CTATTGACTC     540

TACTTCTTTA AAAGCGGCTG CCCATTACAT TCCTCAGCTG TCCTTGCAGT TAGGTGTACA     600
```

-continued

```
TGTGACTGAG TGTTGGCCAG TGAGATGAAG TCTCCTCAAA GGAAGGCAGC ATGTGTCCTT      660

TTTCATCCCT TCATCTTGCT GCTGGGATTG TGGATATAAC AGGAGCCCTG GCAGCTGTCT      720

CCAGAGGATC AAAGCCACAC CCAAAGAGTA AGGCAGATTA GAGACCAGAA AGACCTTGAC      780

TACTTCCCTA CTTCCACTGC TTTTTCCTGC ATTTAAGCCA TTGTAAATCT GGGTGTGTTA      840

CATGAAGTGA AAATTAATTC TTTCTGCCCT TCAGTTCTTT ATCCTGATAC CATTTAACAC      900

TGTCTGAATT AACTAGACTG CAATAATTCT TTCTTTTGAA AGCTTTTAAA GGATAATGTG      960

CAATTCACAT TAAAATTGAT TTTCCATTGT CAATTAGTTA TACTCATTTT CCTGCCTTGA     1020

TCTTTCATTA GATATTTTGT ATCTGCTTGG AATATATTAT CTTCTTTTTA ACTGTGTAAT     1080

TGGTAATTAC TAAAACTCTG TAATCTCCAA AATATTGCTA TCAAATTACA CACCATGTTT     1140

TCTATCATTC TCATAGATCT GCCTTATAAA CATTTAAATA AAAAGTACTA TTTAATGATT     1200

TAAAAAAAAA AAA                                                        1213
```

(2) INFORMATION FOR SEQ ID NO: 4:

(i) SEQUENCE CHARACTERISTICS:
        (A) LENGTH: 1297 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT03
        (B) CLONE: 1999442

(xi) SEQUENCE DESCRIPTION: SEQ ID NO: 4 :

```
CGGACGCGTG GGCTGCTCTG CCTGAGCAAC CTCATGTTTC TGCCACCTGT GGTCCTGGCC       60

ATTCGGAGTC GATATGTGCT GGAAGCTGCA GTCTACACCT TCACCATGTT CTTCTCCACG      120

TTCTATCATG CCTGTGACCA GCCAGGCATC GTGGTTTTCT GCATCATGGA CTACGATGTG      180

CTGCAGTTCT GTGATTTCCT GGGCTCCTTA ATGTCCGTGT GGGTCACTGT CATTGCCATG      240

GCTCGTTTAC AGCCCGTGGT CAAGCAGGTG CTGTATTTGC TGGGAGCTAT GCTGCTGTCC      300

ATGGCTCTGC AGCTTGACCG ACATGGACTC TGGAACCTGC TTGGACCCAG TCTCTTCGCC      360

CTGGGGATCT TGGCCACAGC CTGGACAGTA CGCAGCGTCC GCCGCCGGCA CTGCTACCCA      420

CCCACGTGGC GCCGCTGGCT TTTCTACTTG TGCCCTGGCA GCCTTATTGC AGGCAGTGCC      480

GTCCTGCTTT ATGCTTTTGT GGAGACCCGG GACAACTACT TCTACATTCA CAGCATTTGG      540

CATATGCTCA TTGCGGGCAG TGTGGGCTTC CTGCTGCCCC CTCGTGCCAA GACTGACCAC      600

GGGGTCCCAT CTGGAGCCCG GGCCCGGGGC TGTGGTTACC AGCTATGCAT CAACGAGCAG      660

GAGGAGCCTG GCCTCGTGG GCCCAGGAGG GGCCACTGTC AGCAGCATCT GTGCCAGCTG      720

AGAGGGGCTT TGGGCCTGGC CCTGAGGGGA TATGAATGCT TCCTAGAGTT CTTTCTGGGG      780

GTGTGGAGCC CTCTTAGAAG GAGACAGGCT GTATTTCTTG AGGACATGGA GTCTTTCTCA      840

AGGACACAAA ACTCTTCCAG GGACCTGGAG CCCTTCCCAG GACATGGAGA ACTTCCTGAG      900

GGCCTGGAGT CCCCCTGCAT CATGGAGTCC TTCTTAAGGA CTGGAGCCTA TGCAGGCACA      960

GAGTCCCTCA GGACCAAGGA GTCCCTCCTG CAGGTGTGGA GCCTTTCCTG GGATGCAGAG     1020

CCTTCCCAAG ACATGGATTC CTTCCCAGGG AGACAAAGCC CTGTCAGGAG CACAGCATCT     1080

TTCCAGAGGA GGTGGAGTCT ATCTTGGGGA AACCAAATTT CCAGATTTTC CCAGAGGCTC     1140

AGCAACTCTG GCCTCAGGCT TCCTTCCCAG AGGCAGCGTC TGGGCTGTGC TGTGCTGTGG     1200

AGGAGGGATT GCAGGATGGA TGGAGCTGGG ACTGGGGCTG TCTGGGTGGC TGGTATCCTC     1260
```

```
GTTTGATACA GGTGGAGTCT CTGTGTCTCC ATAGAAG                                    1297

(2) INFORMATION FOR SEQ ID NO:     5:

(i) SEQUENCE CHARACTERISTICS:
        (A) LENGTH: 76 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1216498

(xi) SEQUENCE DESCRIPTION: SEQ ID NO: 5 :

Met Gly Arg Ala Met Val Val Arg Leu Gly Leu Gly Leu Leu Leu
                 5                  10                  15

Leu Ala Leu Leu Leu Pro Thr Gln Ile Tyr Cys Asn Gln Thr Ser
                20                  25                  30

Val Ala Pro Phe Ser Gly Asn Gln Ser Ile Ser Ala Ala Pro Asn
                35                  40                  45

Pro Thr Asn Ala Thr Thr Arg Ser Gly Cys Ser Ser Leu Gln Ser
                50                  55                  60

Thr Ala Gly Leu Leu Ala Leu Ser Leu Ser Leu Leu His Leu Tyr
                65                  70                  75

Cys (2) INFORMATION FOR SEQ ID NO:     6:

(i) SEQUENCE CHARACTERISTICS:
        (A) LENGTH: 261 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 130989

(xi) SEQUENCE DESCRIPTION: SEQ ID NO: 6 :

Met Trp Val Pro Val Val Phe Leu Thr Leu Ser Val Thr Trp Ile
                 5                  10                  15

Gly Ala Ala Pro Leu Ile Leu Ser Arg Ile Val Gly Gly Trp Glu
                20                  25                  30

Cys Glu Lys His Ser Gln Pro Trp Gln Val Leu Val Ala Ser Arg
                35                  40                  45

Gly Arg Ala Val Cys Gly Gly Val Leu Val His Pro Gln Trp Val
                50                  55                  60

Leu Thr Ala Ala His Cys Ile Arg Asn Lys Ser Val Ile Leu Leu
                65                  70                  75

Gly Arg His Ser Leu Phe His Pro Glu Asp Thr Gly Gln Val Phe
                80                  85                  90

Gln Val Ser His Ser Phe Pro His Pro Leu Tyr Asp Met Ser Leu
                95                 100                 105

Leu Lys Asn Arg Phe Leu Arg Pro Gly Asp Asp Ser Ser His Asp
               110                 115                 120

Leu Met Leu Leu Arg Leu Ser Glu Pro Ala Glu Leu Thr Asp Ala
               125                 130                 135

Val Lys Val Met Asp Leu Pro Thr Gln Glu Pro Ala Leu Gly Thr
               140                 145                 150
```

```
Thr Cys Tyr Ala Ser Gly Trp Gly Ser Ile Glu Pro Glu Glu Phe
                155                 160                 165

Leu Thr Pro Lys Lys Leu Gln Cys Val Asp Leu His Val Ile Ser
                170                 175                 180

Asn Asp Val Cys Ala Gln Val His Pro Gln Lys Val Thr Lys Phe
                185                 190                 195

Met Leu Cys Ala Gly Arg Trp Thr Gly Gly Lys Ser Thr Cys Ser
                200                 205                 210

Gly Asp Ser Gly Gly Pro Leu Val Cys Asn Gly Val Leu Gln Gly
                215                 220                 225

Ile Thr Ser Trp Gly Ser Glu Pro Cys Ala Leu Pro Glu Arg Pro
                230                 235                 240

Ser Leu Tyr Thr Lys Val Val His Tyr Arg Lys Trp Ile Lys Asp
                245                 250                 255

Thr Ile Val Ala Asn Pro
                260

(2) INFORMATION FOR SEQ ID NO:      7:

(i) SEQUENCE CHARACTERISTICS:
        (A) LENGTH: 1317 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2459993

(xi) SEQUENCE DESCRIPTION: SEQ ID NO: 7 :

Met Leu Ala Cys Leu Cys Cys Lys Lys Gly Gly Ile Gly Phe Lys
                 5                  10                  15

Glu Phe Glu Asn Ala Glu Gly Asp Glu Tyr Val Ala Asp Phe Ser
                20                  25                  30

Glu Gln Gly Ser Pro Ala Ala Ala Ala Gln Thr Gly Pro Asp Val
                35                  40                  45

Tyr Val Leu Pro Leu Thr Glu Val Ser Leu Pro Met Ala Lys Gln
                50                  55                  60

Pro Gly Arg Ser Val Gln Leu Leu Lys Ser Thr Asp Leu Gly Arg
                65                  70                  75

His Ser Leu Leu Tyr Leu Lys Glu Ile Gly His Gly Trp Phe Gly
                80                  85                  90

Lys Val Phe Leu Gly Glu Val His Ser Gly Val Ser Gly Thr Gln
                95                  100                 105

Val Val Val Lys Glu Leu Lys Val Ser Ala Ser Val Gln Glu Gln
                110                 115                 120

Met Gln Phe Leu Glu Glu Ala Gln Pro Tyr Arg Ala Leu Gln His
                125                 130                 135

Ser Asn Leu Leu Gln Cys Leu Ala Gln Cys Ala Glu Val Thr Pro
                140                 145                 150

Tyr Leu Leu Val Met Glu Phe Cys Pro Leu Gly Asp Leu Lys Gly
                155                 160                 165

Tyr Leu Arg Ser Cys Arg Val Thr Glu Ser Met Ala Pro Asp Pro
                170                 175                 180

Leu Thr Leu Gln Arg Met Ala Cys Glu Val Ala Cys Gly Val Leu
                185                 190                 195
```

-continued

```
His Leu His Arg His Asn Tyr Val His Ser Asp Leu Ala Leu Arg
                200                 205                 210

Asn Cys Leu Leu Thr Ala Asp Leu Thr Val Lys Val Gly Asp Tyr
                215                 220                 225

Gly Leu Ser His Cys Lys Tyr Arg Glu Asp Tyr Leu Val Thr Ala
                230                 235                 240

Asp Gln Leu Trp Val Pro Leu Arg Trp Ile Ala Pro Glu Leu Val
                245                 250                 255

Asp Glu Val His Gly Asn Leu Leu Val Val Asp Gln Thr Lys Ser
                260                 265                 270

Ser Asn Val Trp Ser Leu Gly Val Thr Ile Trp Glu Leu Phe Glu
                275                 280                 285

Leu Gly Ala Gln Pro Tyr Pro Gln His Ser Asp Arg Gln Val Leu
                290                 295                 300

Ala Tyr Ala Val Arg Glu Gln Gln Leu Lys Leu Pro Lys Pro Gln
                305                 310                 315

Leu Gln Leu Ala Leu Ser Asp Arg Trp Tyr Glu Val Met Gln Phe
                320                 325                 330

Cys Trp Leu Gln Pro Glu Gln Arg Pro Thr Ala Glu Val His
                335                 340                 345

Leu Leu Leu Ser Tyr Leu Cys Ala Lys Gly Thr Thr Glu Leu Glu
                350                 355                 360

Glu Glu Phe Glu Arg Arg Trp Arg Ser Leu Arg Pro Gly Gly Ser
                365                 370                 375

Thr Gly Leu Gly Ser Gly Ser Ala Ala Pro Ala Ala Thr Ala
                380                 385                 390

Ala Ser Ala Glu Leu Thr Ala Ala Ser Ser Phe Pro Leu Leu Glu
                395                 400                 405

Arg Phe Thr Ser Asp Gly Phe His Val Asp Ser Asp Val Leu
                410                 415                 420

Thr Val Thr Glu Thr Ser His Gly Leu Asn Phe Glu Tyr Lys Trp
                425                 430                 435

Glu Ala Gly Cys Gly Ala Glu Glu Tyr Pro Pro Ser Gly Ala Ala
                440                 445                 450

Ser Ser Pro Gly Ser Ala Ala Arg Leu Gln Glu Leu Cys Ala Pro
                455                 460                 465

Asp Ser Ser Pro Pro Gly Val Val Pro Val Leu Ser Ala His Ser
                470                 475                 480

Pro Ser Val Gly Ser Glu Tyr Phe Ile Arg Leu Glu Gly Ala Val
                485                 490                 495

Pro Ala Ala Gly His Asp Pro Asp Cys Ala Gly Cys Ala Pro Ser
                500                 505                 510

Pro Gln Ala Val Thr Asp Gln Asp Asn Asn Ser Glu Glu Ser Thr
                515                 520                 525

Val Ala Ser Leu Ala Met Glu Pro Leu Leu Gly His Ala Pro Pro
                530                 535                 540

Thr Glu Gly Leu Trp Gly Pro Cys Asp His His Ser His Arg Arg
                545                 550                 555

Gln Gly Ser Pro Cys Pro Ser Arg Ser Pro Ser Pro Gly Thr Pro
                560                 565                 570

Met Leu Pro Ala Glu Asp Ile Asp Trp Gly Val Ala Thr Phe Cys
                575                 580                 585

Pro Pro Phe Phe Asp Asp Pro Leu Gly Ala Ser Pro Ser Gly Ser
```

-continued

```
                590                 595                 600
Pro Gly Ala Gln Pro Ser Pro Ser Asp Glu Glu Pro Glu Glu Gly
                605                 610                 615
Lys Val Gly Leu Ala Ala Gln Cys Gly His Trp Ser Ser Asn Met
                620                 625                 630
Ser Ala Asn Asn Asn Ser Ala Ser Arg Asp Pro Glu Ser Trp Asp
                635                 640                 645
Pro Gly Tyr Val Ser Ser Phe Thr Asp Ser Tyr Arg Asp Asp Cys
                650                 655                 660
Ser Ser Leu Glu Gln Thr Pro Arg Ala Ser Pro Glu Val Gly His
                665                 670                 675
Leu Leu Ser Gln Glu Asp Pro Arg Asp Phe Leu Pro Gly Leu Val
                680                 685                 690
Ala Val Ser Pro Gly Gln Glu Pro Ser Arg Pro Phe Asn Leu Leu
                695                 700                 705
Pro Leu Cys Pro Ala Lys Gly Leu Ala Pro Ala Ala Cys Leu Ile
                710                 715                 720
Thr Ser Pro Trp Thr Glu Gly Ala Val Gly Gly Ala Glu Asn Pro
                725                 730                 735
Ile Val Glu Pro Lys Leu Ala Gln Glu Ala Glu Gly Ser Ala Glu
                740                 745                 750
Pro Gln Leu Pro Leu Pro Ser Val Pro Ser Pro Ser Cys Glu Gly
                755                 760                 765
Ala Ser Leu Pro Ser Glu Glu Ala Ser Ala Pro Asp Ile Leu Pro
                770                 775                 780
Ala Ser Pro Thr Pro Ala Ala Gly Ser Trp Val Thr Val Pro Glu
                785                 790                 795
Pro Ala Pro Thr Leu Glu Ser Ser Gly Ser Ser Leu Gly Gln Glu
                800                 805                 810
Ala Pro Ser Ser Glu Asp Glu Asp Thr Thr Glu Ala Thr Ser Gly
                815                 820                 825
Val Phe Thr Asp Leu Ser Ser Asp Gly Pro His Thr Glu Lys Ser
                830                 835                 840
Gly Ile Val Pro Ala Leu Arg Ser Leu Gln Lys Gln Val Gly Thr
                845                 850                 855
Pro Asp Ser Leu Asp Ser Leu Asp Ile Pro Ser Ser Ala Ser Asp
                860                 865                 870
Gly Gly Cys Glu Val Leu Ser Pro Ser Ala Ala Gly Pro Pro Gly
                875                 880                 885
Gly Gln Pro Arg Ala Val Asp Ser Gly Tyr Asp Thr Glu Asn Tyr
                890                 895                 900
Glu Ser Pro Glu Phe Val Leu Lys Glu Ala His Glu Ser Ser Glu
                905                 910                 915
Pro Glu Ala Phe Gly Glu Pro Ala Ser Glu Gly Ser Pro Gly
                920                 925                 930
Pro Asp Pro Leu Leu Ser Val Ser Leu Gly Gly Leu Ser Lys Lys
                935                 940                 945
Ser Pro Tyr Arg Asp Ser Ala Tyr Phe Ser Asp Leu Asp Ala Glu
                950                 955                 960
Ser Glu Pro Thr Phe Gly Pro Glu Lys His Ser Gly Ile Gln Asp
                965                 970                 975
```

-continued

```
Ser Gln Lys Glu Gln Asp Leu Arg Ser Pro Pro Ser Pro Gly His
                980                 985                 990

Gln Ser Val Gln Ala Phe Pro Arg Ser Ala Val Ser Ser Glu Val
                995                1000                1005

Leu Ser Pro Pro Gln Gln Ser Glu Glu Pro Leu Pro Glu Val Pro
               1010                1015                1020

Arg Pro Glu Pro Leu Gly Ala Gln Gly Pro Val Gly Val Gln Pro
               1025                1030                1035

Val Pro Gly Pro Ser His Ser Lys Cys Phe Pro Leu Thr Ser Val
               1040                1045                1050

Pro Leu Ile Ser Glu Gly Ser Gly Thr Glu Pro Gln Gly Pro Ser
               1055                1060                1065

Gly Gln Leu Ser Gly Arg Ala Gln Gln Gly Gln Met Gly Asn Pro
               1070                1075                1080

Ser Thr Pro Arg Ser Pro Leu Cys Leu Ala Leu Pro Gly His Pro
               1085                1090                1095

Gly Ala Leu Glu Gly Arg Pro Glu Glu Asp Glu Asp Thr Glu Asp
               1100                1105                1110

Ser Glu Glu Ser Asp Glu Glu Leu Arg Cys Tyr Ser Val Gln Glu
               1115                1120                1125

Pro Ser Glu Asp Ser Glu Glu Glu Pro Pro Ala Val Pro Val Val
               1130                1135                1140

Val Ala Glu Ser Gln Ser Ala Arg Asn Leu Arg Ser Leu Leu Lys
               1145                1150                1155

Met Pro Ser Leu Leu Ser Glu Ala Phe Cys Asp Asp Leu Glu Arg
               1160                1165                1170

Lys Lys Lys Ala Val Ser Phe Phe Asp Asp Val Thr Val Tyr Leu
               1175                1180                1185

Phe Asp Gln Glu Ser Pro Thr Arg Glu Thr Gly Glu Pro Phe Pro
               1190                1195                1200

Ser Thr Lys Glu Ser Leu Pro Thr Phe Leu Glu Gly Gly Pro Ser
               1205                1210                1215

Ser Pro Ser Ala Thr Gly Leu Pro Leu Arg Ala Gly His Ser Pro
               1220                1225                1230

Asp Ser Ser Ala Pro Glu Pro Gly Ser Arg Phe Glu Trp Asp Gly
               1235                1240                1245

Asp Phe Pro Leu Val Pro Gly Lys Ala Ala Leu Val Thr Glu Leu
               1250                1255                1260

Asp Pro Ala Asp Pro Val Leu Ala Ala Pro Pro Thr Pro Ala Ala
               1265                1270                1275

Pro Phe Ser Arg Phe Thr Val Ser Pro Thr Pro Ala Ser Arg Phe
               1280                1285                1290

Ser Ile Thr His Ile Ser Asp Ser Asp Ala Gln Ser Val Gly Gly
               1295                1300                1305

Pro Ala Ala Gly Ala Gly Gly Arg Tyr Thr Glu Ala
               1310                1315
```